United States Patent
Noda (10) Patent No.: US 12,402,849 B2
(45) Date of Patent: Sep. 2, 2025

(54) X-RAY DIAGNOSTIC APPARATUS

(71) Applicant: CANON MEDICAL SYSTEMS CORPORATION, Tochigi (JP)

(72) Inventor: Koji Noda, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 169 days.

(21) Appl. No.: 18/057,882

(22) Filed: Nov. 22, 2022

(65) Prior Publication Data

US 2023/0157655 A1    May 25, 2023

(30) Foreign Application Priority Data

Nov. 25, 2021  (JP) ................................. 2021-190923

(51) Int. Cl.
*A61B 6/00*    (2006.01)

(52) U.S. Cl.
CPC .................. *A61B 6/4441* (2013.01)

(58) Field of Classification Search
CPC .................................................. A61B 6/4441
See application file for complete search history.

(56) References Cited

U.S. PATENT DOCUMENTS

| | | | |
|---|---|---|---|
| 9,801,598 B2 | 10/2017 | Zaiki et al. | |
| 2008/0317199 A1 | 12/2008 | Van Der Ende | |
| 2015/0157283 A1 | 6/2015 | Zaiki et al. | |
| 2015/0313564 A1* | 11/2015 | Narabu | A61B 6/022 378/42 |
| 2016/0015345 A1* | 1/2016 | Noda | A61B 6/504 378/197 |

FOREIGN PATENT DOCUMENTS

| | | |
|---|---|---|
| JP | 2007-521857 A | 8/2007 |
| JP | 2015-131088 A | 7/2015 |

* cited by examiner

*Primary Examiner* — Hugh Maupin
(74) *Attorney, Agent, or Firm* — Oblon, McClelland, Maier & Neustadt, L.L.P.

(57) ABSTRACT

An X-ray diagnostic apparatus according to an embodiment includes an arm, a first holder, a second holder, a driver, and a third holder. The arm has the shape of a circular arc; supports an X-ray tube and an X-ray detector. The first holder grasps the arm in a movable manner in the circular arc direction. The second holder supports the first holder in a movable manner in the circular arc direction. The driver is disposed in the second holder; moves the first holder; and, at the same time, relatively moves the arm with respect to the first holder. The third holder is orthogonal to the rotation axis involved in the movement of the arm in the circular arc direction and holds the second holder in a rotatable manner with the axis substantially orthogonal to the vertical direction serving as the rotation axis.

9 Claims, 9 Drawing Sheets

X-RAY DIAGNOSTIC APPARATUS

CROSS-REFERENCE TO RELATED APPLICATIONS

This application is based upon and claims the benefit of priority from Japanese Patent Application No. 2021-190923, filed on Nov. 25, 2021; the entire contents of which are incorporated herein by reference.

FIELD

Embodiments described herein relate generally to an X-ray diagnostic apparatus.

BACKGROUND

Some X-ray diagnostic apparatuses include an X-ray tube; an X-ray detector; and a C-arm or an Ω-arm that has the shape of a circular arc and that supports the X-ray tube and the X-ray detector to be at opposed positions. In such an X-ray diagnostic apparatus, the C-arm or the Ω-arm is made to perform a sliding movement in the circular arc direction around the subject, so that three-dimensional imaging can be performed. Herein, in order to perform three-dimensional imaging and collect three-dimensional image data, for example, it is desirable that the imaging range equal to or greater than 180° is secured around the subject.

Thus, in the X-ray diagnostic apparatus, it is necessary to secure a wide range (stroke) within which the arm is slidable. As a configuration satisfying such a requirement, for example, it is possible to think of an X-ray diagnostic apparatus that includes a plurality of arms (a first arm and a second arm) configured to be slidable in the same circular arm direction. In that case, the first arm is, for example, a C-arm that supports the X-ray tube and the X-ray detector and that performs the sliding movement in a circular arc direction. The second arm holds the first arm and performs the sliding movement in the same direction as the sliding direction of the first arm. With that, it becomes possible to widen the stroke of the C-arm, thereby enabling securing a wider imaging range. Meanwhile, in the present written description, the structure including such plurality of arms is called a double-slide structure.

DETAILED DESCRIPTION

An X-ray diagnostic apparatus according to an embodiment includes an arm, a first holder, a second holder, a driver, and a third holder. The arm has the shape of a circular arc; supports, at one end thereof, an X-ray tube which emits X-rays onto a subject; and supports, at the other end thereof, an X-ray detector which detects X-rays that have passed through the subject. The first holder grasps the arm in a movable manner in the circular arc direction. The second holder supports the first holder in a movable manner in the circular arc direction. The driver is disposed in the second holder; moves the first holder; and, at the same time, relatively moves the arm with respect to the first holder. The third holder is orthogonal to the rotation axis involved in the movement of the arm in the circular arc direction and holds the second holder in a rotatable manner with the axis substantially orthogonal to the vertical direction serving as the rotation axis.

Exemplary embodiments of an X-ray diagnostic apparatus are described below in detail with reference to the accompanying drawings. However, the X-ray diagnostic apparatus according to the application concerned is not limited by the embodiments described below. In the following explanation, identical constituent elements are referred to by the same reference numerals, and their explanation is not repeated.

First Embodiment

Figure 1:
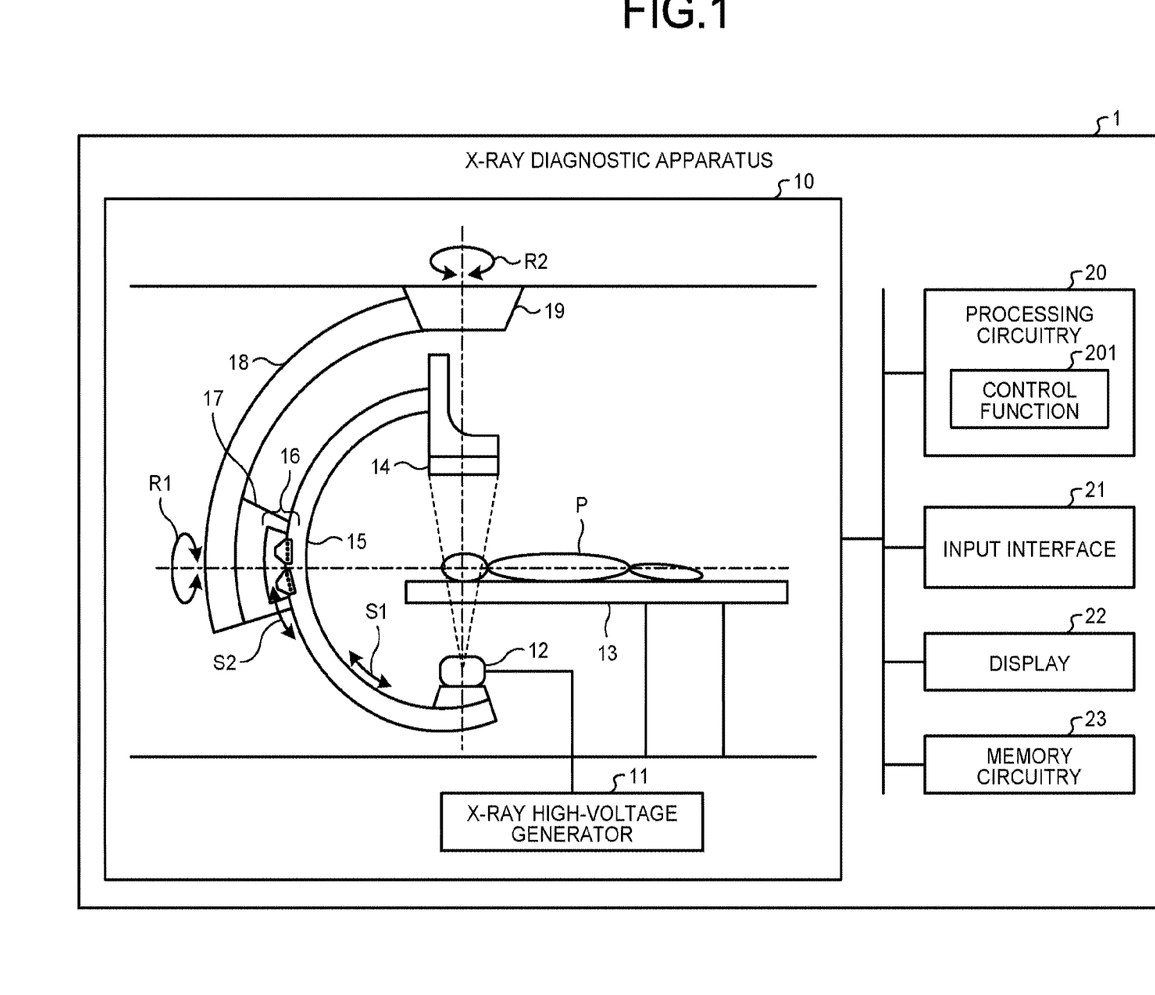
FIG. 1 is a block diagram illustrating an exemplary configuration of an X-ray diagnostic apparatus according to a first embodiment.

FIG. 1 is a block diagram illustrating an exemplary configuration of an X-ray diagnostic apparatus 1 according to a first embodiment. As illustrated in FIG. 1, the X-ray diagnostic apparatus 1 includes an imaging unit 10, processing circuitry 20, an input interface 21, a display 22, and memory circuitry 23. The following explanation is given about an example in which the X-ray diagnostic apparatus 1 has a suspension mechanism (a suspended-type X-ray diagnostic apparatus) for keeping some part of the imaging unit 10 suspended from the ceiling. Moreover, the following explanation is given about an example in which the X-ray diagnostic apparatus 1 is of the single-plane type. However, the embodiments are not limited to that case, and alternatively the X-ray diagnostic apparatus 1 can be of the biplane type.

The imaging unit 10 includes an X-ray high-voltage generator 11, an X-ray tube 12, a couchtop 13, an X-ray detector 14, a C-arm 15, roller units 16, a holder 17, a ceiling-type rotating arm 18, and a ceiling-type rotating arm supporting member 19. The imaging unit 10 emits X-rays onto a subject P, and detects the X-rays that have passed through the subject P.

The X-ray high-voltage generator 11 generates a high voltage under the control of the processing circuitry 20, and applies the high voltage to the X-ray tube 12. Based on the high voltage applied by the X-ray high-voltage generator 11, the X-ray tube 12 emits X-rays toward the subject P who is present on the couchtop 13. Moreover, in the X-ray tube 12, an X-ray aperture (not illustrated) is included on the plane opposite to the subject P. Under the control of the processing circuitry 20, the X-ray aperture opens and closes the aperture blade, and forms an exposure range (exposure field) of the X-rays emitted from the X-ray tube 12. For example, the aperture blade is formed in the shape of a plate using an X-ray shielding material such as lead. The couchtop 13 is a bed on which the subject P is asked to lie down, and is placed on top of a couch (not illustrated).

The X-ray detector 14 is an X-ray flat plane detector (FPD) in which, for example, radiation detecting elements are arranged in a matrix. The X-ray detector 14 detects X-rays that, after being emitted from the X-ray tube 12, have passed through the subject P; and outputs detection signals according to the detected X-ray dosage (i.e., outputs X-ray detection signals) to the processing circuitry 20.

The C-arm 15 has the shape of a circular arc. At one end thereof, the C-arm 15 supports the X-ray tube 12; and, at the other end thereof, the C-arm 15 supports the X-ray detector 14. Thus, the C-arm 15 supports the X-ray tube 12 and the X-ray detector 14 across the subject P. Moreover, the C-arm 15 supports the X-ray tube 12 and the X-ray detector 14 in an independently-rotatable manner. On the lateral face opposite to the inside face on which the X-ray tube and the X-ray detector 14 are disposed, the C-arm 15 includes U-shaped rails that move while making contact with wheels 161 of the roller units 16 (explained later). As a result, the C-arm 15 moves in a circular arc direction indicated by an arrow S1 illustrated in FIG. 1. Herein, the C-arm 15 represents an example of an arm.

The roller units 16 grasp the C-arm 15 and enable the sliding movement of the C-arm 15 in the circular arc direction indicated by the arrow S1 illustrated in FIG. 1. Moreover, the roller units 16 are supported by the holder 17, and are capable of performing the sliding movement when a driving unit (explained later) runs them on the rails of the C-arm 15 in the circular arc direction indicated by an arrow S2 illustrated in FIG. 1. The roller units 16 represent an example of a first holder.

The holder 17 has a driving unit installed therein, and supports the roller units 16 in a slidable manner in the circular arc direction illustrated by the arrow S2. Moreover, at the lower end of the ceiling-type rotating arm 18, the holder 17 is pivotally supported to be rotatable around a rotation axis R1 illustrated in FIG. 1. The holder 17 represents an example of a second holder.

The driving unit includes roller unit driving gears 31 (explained later), a timing belt driving pulley 32 (explained later), and a shaft 33 (explained later). The driving unit is disposed inside the holder 17 and, under the control of the processing circuitry 20 (explained later), drives the imaging unit 10 by transmitting power that comes from a power source such as a motor (not illustrated) or an actuator (not illustrated). For example, the driving unit causes the C-arm 15 and the roller units 16 to perform the sliding movement/rotation. The driving unit represents an example of a driver.

The rotation axis R1 is positioned at the center of the holder 17 and at the lower end of the ceiling-type rotating arm 18, and represents the rotation axis for the rotation of the holder 17 with respect to the ceiling-type rotating arm 18. More particularly, the rotation axis R1 is orthogonal to the rotation axis during the sliding movement of the C-arm 15, and is also orthogonal to the vertical direction (gravity direction). When the holder 17 rotates around the rotation axis R1; the roller units 16, which are supported by the holder 17, and the C-arm 15, which is supported by the roller units 16, rotate along with the holder 17 around the rotation axis R1.

The ceiling-type rotating arm 18 has the shape of a circular arc and, at the lower end thereof, supports the holder 17 in a rotatable manner around the rotation axis R1. Thus, the ceiling-type rotating arm 18 holds the holder 17 in a rotatable manner with the rotation axis R1 serving as the rotation axis. Moreover, at the upper end thereof, the ceiling-type rotating arm 18 is supported by the ceiling-type rotating arm supporting member 19 in a gyratable manner around a rotation axis R2. The ceiling-type rotating arm 18 represents an example of a third holder.

The ceiling-type rotating arm supporting member 19 is installed on the ceiling of the inspection room. The ceiling-type rotating arm supporting member 19 supports the ceiling-type rotating arm 18 in a gyratable manner around the rotation axis R2. The rotation axis R2 is orthogonal to the ceiling or the floor, and is also orthogonal to the rotation axis R1.

The processing circuitry 20 is configured using, for example, a processor. The processing circuitry 20 controls a control function 201 for controlling the entire X-ray diagnostic apparatus 1. More particularly, the control function 201 supplies control signals to the X-ray high-voltage generator 11, the X-ray tube 12, the X-ray aperture, the couchtop 13, the X-ray detector 14, the C-arm 15, the roller units 16, the holder 17, the ceiling-type rotating arm 18, and the ceiling-type rotating arm supporting member 19; so that X-ray radiation is carried out. The control function 201 represents an example of a control unit. Regarding the control function 201, the detailed explanation is given later.

The input interface 21 is configured using an input device that receives various input operations from the user. The input interface 21 receives an input operation from the user, and outputs an electrical signal corresponding to the received input operation to the processing circuitry 20. For example, the input interface 21 includes a mouse, a keyboard, or a trackball. Alternatively, the input interface 21 includes a hand-switch (an exposure switch) or a foot-switch as an operation button for receiving an operation from the user. Still alternatively, the input interface 21 can be configured using a touchpad in which an input operation is performed by touching the operation screen; or using a contactless input circuit in which an optical sensor is used; or using a voice input circuit. The input interface 21 can also be configured using a tablet terminal capable of performing wireless communication with the device main body. Meanwhile, the input interface 21 is not limited to include a physical operation component such as a mouse or keyboard. That is, examples of the input interface 21 also include an electrical signal processing circuit that receives an electrical signal corresponding to an input operation from an external input device installed separately from the device, and that outputs the electrical signal to the processing circuitry 20.

The display 22 is configured using a display device that displays a variety of information. For example, the display 22 displays a graphical user interface (GUI) and collected X-ray images (fluoroscopic images or photographed images) of the subject P.

The memory circuitry 23 is configured using, for example, a semiconductor memory device such as a random access memory (RAM) or a flash memory; or a hard disk; or an optical disk. The memory circuitry 23 is used to store a variety of information used in or generated by the processing circuitry 20. For example, the memory circuitry 23 is used to store a variety of information such as X-ray images of the subject P and a GUI. Moreover, the memory circuitry 23 is used to store a computer program that causes the processing circuitry 20 to function as the control function 201.

Till now, the explanation was given about an exemplary configuration of the X-ray diagnostic apparatus 1 according to the first embodiment. With such a configuration, the X-ray diagnostic apparatus 1 enables expanding the slidable range of the arm while holding down an increase in the apparatus size. More particularly, in the X-ray diagnostic apparatus 1, accompanying the sliding movement of the C-arm 15, the roller units 16 made to slide in the same circular arc direction as the direction of the sliding movement of the C-arm 15. With that, the stroke of the C-arm 15 can be widened while preventing an increase in the apparatus size.

In the X-ray diagnostic apparatus 1, the X-ray tube 12 and the X-ray detector 14 are supported by the C-arm 15, and the C-arm 15 is made to slide along a circular arc. With that, the X-ray tube 12 and the X-ray detector 14 are made to slide to the positions along the circular arc of the C-arm 15. At that time, the X-ray diagnostic apparatus 1 can perform rotational transverse tomography in which images of the subject P are taken at every position (each photographing angle) along the circular arc of the C arm 15. As a result, the X-ray diagnostic apparatus 1 can collect projection data at each photographing angle; perform three-dimensional reconstruction; and obtain three-dimensional images. However, in order to perform the three-dimensional reconstruction in an appropriate manner, the projection data needs to be collected at the photographing angles equal to or greater than 180° around the subject P. That is, an imaging system made up of the X-ray tube 12, the X-ray detector 14, and the C-arm 15 is required to be able to perform the sliding movement over 180° or more.

Figure 2:
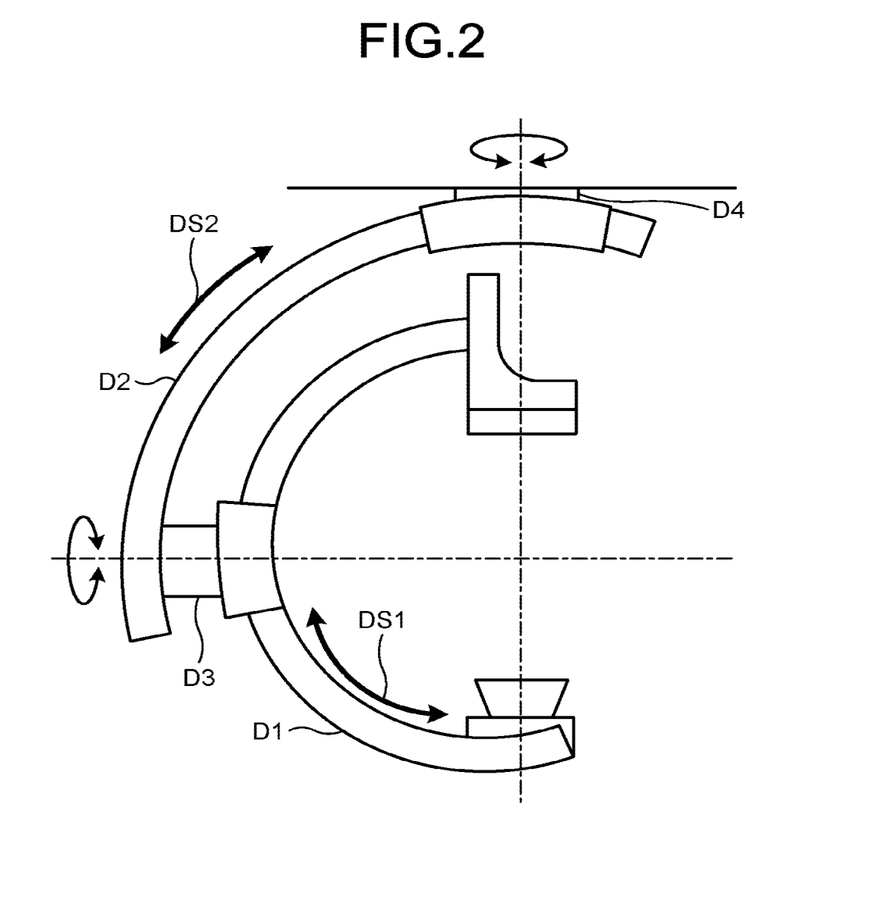
FIG. 2 is a diagram for explaining a double-slide structure.

In that regard, in order to widen the stroke of the C-arm 15 that supports the X-ray tube 12 and the X-ray detector 14, it is possible to think of an X-ray diagnostic apparatus that includes a plurality of arms capable of performing the sliding movement in the same circular arc direction. FIG. 2 is a diagram illustrating an example of an X-ray diagnostic apparatus having the double-slide structure. With reference to FIG. 2, a suspended-type X-ray diagnostic apparatus includes a first arm D1 and a second arm D2. The first arm D1 supports an X-ray tube and an X-ray detector, and performs the sliding movement in the circular arc direction indicated by an arrow DS1 illustrated in FIG. 2. The second arm D2 holds the first arm D1 via a holder D3 provided for support at the lower end, and performs the sliding movement in the same direction as the direction of the sliding direction of the first arm D1. Moreover, the second arm D2 is pivotally supported by a supporting member D4 that is installed on the ceiling of the examination room.

However, the structure of the X-ray diagnostic apparatus as illustrated in FIG. 2 may become large in size and complex. More particularly, in the case of using a plurality of sliding arms, as compared to an X-ray diagnostic apparatus that includes only a C-arm as a sliding arm, sometimes there is an increase in the overall size of the X-ray diagnostic apparatus in order to support the moment load during the sliding movement. Moreover, in the case of using a plurality of sliding arms, it may lead to an increase in the occupancy of the X-ray diagnostic apparatus in the examination room in which it is installed. Furthermore, in an X-ray diagnostic apparatus having the double-slide structure, a plurality of arms is made to slide in the same circular arc direction while supporting them. As a result, the internal structure becomes complex.

Moreover, it is possible to think that, when the apparatus structure becomes large and complex, it impairs the accessibility inside the examination room. For example, a situation may arise in which it is difficult to confirm the other devices, the subject, and the healthcare personnel present around the concerned device in the examination room.

In that regard, in the X-ray diagnostic apparatus 1 according to the first embodiment, accompanying the sliding movement of the C-arm 15, the roller units 16 are made to slide in the same circular arc direction as the C-arm 15. As a result, the stroke of the C-arm 15 can be widened while avoiding an increase in the size of the X-ray diagnostic apparatus 1.

Figure 3:
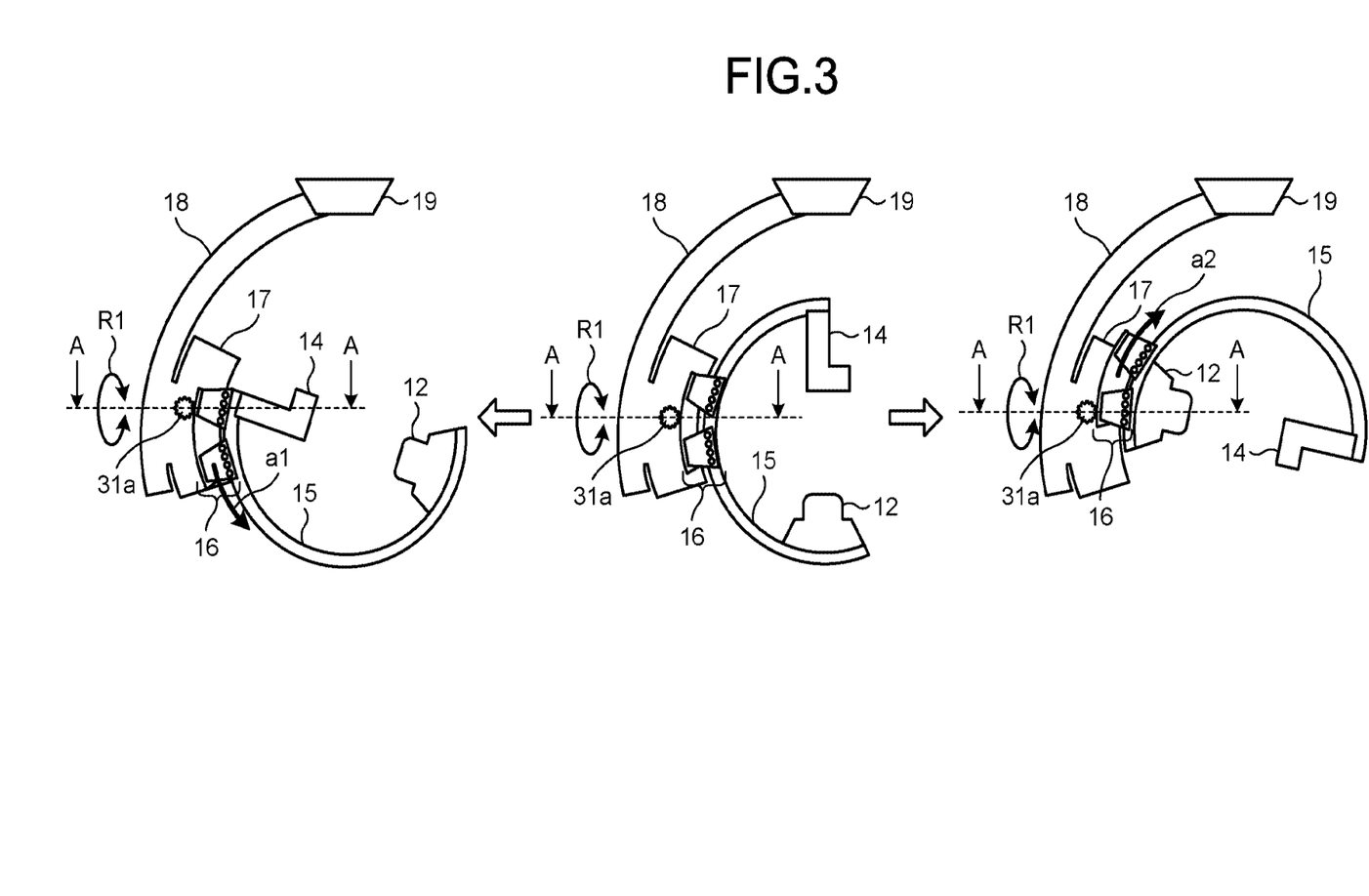
FIG. 3 is a diagram illustrating the movements occurring in the X-ray diagnostic apparatus according to the first embodiment.

FIG. 3 is a diagram illustrating the movements occurring in the X-ray diagnostic apparatus 1 according to the first embodiment. In FIG. 3 is illustrated the transition among three types of C-arm holding states in the X-ray diagnostic apparatus 1. More particularly, in the central drawing in FIG. 3, a first holding state is illustrated in which the roller units 16 fit inside the holder 17 and in which the middle portion between the roller units 16 is coincident with the rotation axis R1. In the left-side drawing in FIG. 3, a second holding state is illustrated in which, with reference to the first holding state, the C-arm 15 and the roller units 16 are made to slide in the direction indicated by an arrow a1, so that the X-ray tube 12 moves away from the holder 17. In the right-side drawing in FIG. 3, a third holding state is illustrated in which the C-arm 15 and the roller units 16 are made to slide in the direction indicated by an arrow a2, so that the X-ray tube 12 moves closer to the holder 17. In the second holding state and the third holding state, the amount of sliding movement of the C-arm 15 and the roller units 16 is maximum.

For example, in the X-ray diagnostic apparatus 1, as illustrated in the second holding state (the left-side drawing in FIG. 3), during the sliding movement of the C-arm 15 in the direction of the arrow a1, the roller units 16 perform the sliding movement in the same direction (the direction indicated by the arrow a1) up to the position of being pushed out from the holder 17. As a result, in the X-ray diagnostic apparatus 1, as compared to the case in which only the C-arm 15 performs the sliding movement in the same direction as explained above, regarding the sliding movement of the X-ray tube 12 in the direction away from the holder 17, the stroke can be widened by the amount equivalent to the amount of sliding movement of the roller units 16. Meanwhile, the roller units 16 perform the sliding movement due to the driving force transmitted thereto from a roller unit driving gear 31a that is disposed on the rotation axis R1. In this case, for the purpose of engaging with the roller unit driving gear 31a, the roller units 16 are provided with a gear on the side of the roller unit driving gear 31a. Thus, due to the driving force transmitted from the roller unit driving gear 31a, the roller units 16 perform the sliding movement.

In an identical manner, for example, in the X-ray diagnostic apparatus 1, as illustrated in the third holding state (the right-side drawing in FIG. 3), during the sliding movement of the C-arm 15 in the direction indicated by the arrow a2, the roller units 16 perform the sliding movement in the same direction (the direction indicated by the arrow a2) up to the position of being pushed out from the holder 17. As a result, in the X-ray diagnostic apparatus 1, as compared to the case in which only the C-arm 15 performs the sliding movement in the same direction, regarding the sliding movement of the X-ray tube 12 in the direction toward the holder 17, the stroke can be widened by the amount equivalent to the amount of sliding movement of the roller units 16. Meanwhile, in an identical manner to the explanation given above, the roller units 16 perform the sliding movement due to the driving force transmitted thereto from the roller unit driving gear 31a disposed on the rotation axis R1.

Figure 4A:
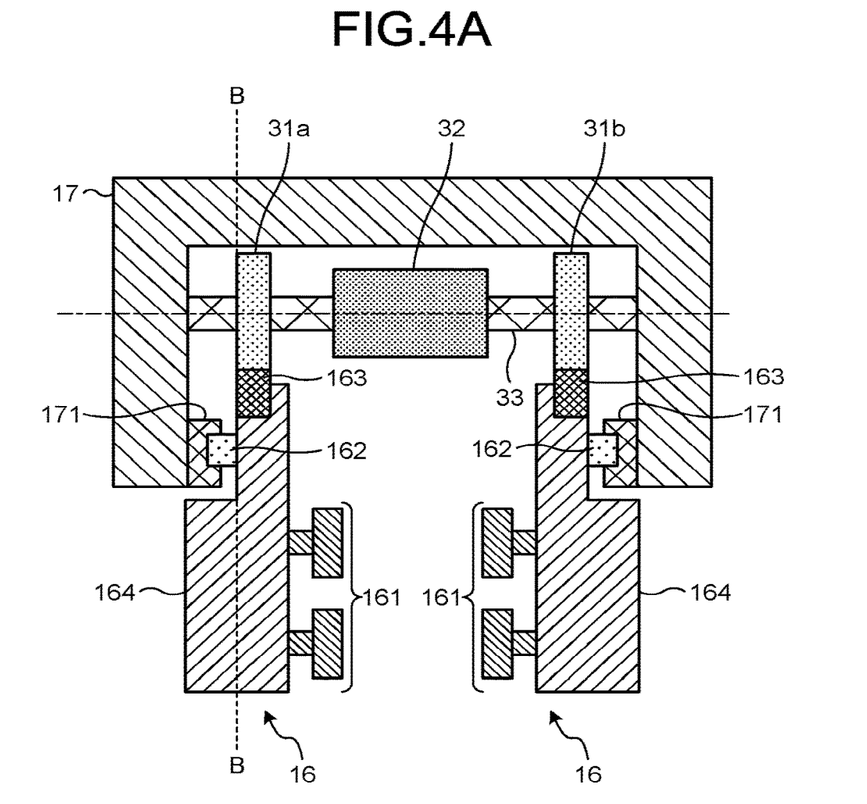
FIGS. 4A and 4B are cross-sectional views illustrating an exemplary structure of an imaging unit according to the first embodiment.
Figure 4B:
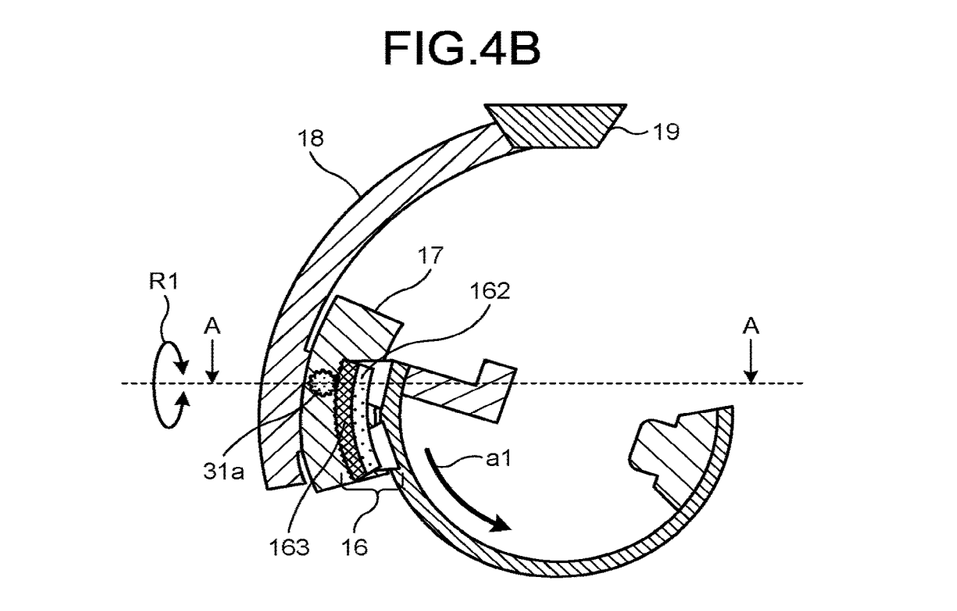

As explained above, in the X-ray diagnostic apparatus 1, the roller units 16 that grasp the C-arm 15 perform the sliding movement in the same direction as the direction of the sliding movement of the C-arm 15. As a result, it becomes possible to widen the stroke. In that regard, in the X-ray diagnostic apparatus 1 according to the first embodiment, because of the structure of the imaging unit 10 explained below in detail, the sliding movement of the C-arm 15 and the sliding movement of the roller units 16 are driven using the same driving force. Given below is the detailed explanation of the structure of the imaging unit 10. FIGS. 4A and 4B are cross-sectional views illustrating an exemplary structure of the imaging unit 10 according to the first embodiment. In FIG. 4A is illustrated the cross-sectional surface in the axis direction of the rotation axis R1 (i.e., an A-A cross-sectional surface). In FIG. 4B is illustrated a B-B cross-sectional surface of FIG. 4A.

As illustrated in FIG. 4A, the holder 17 has blocks 171 fixed therein. Moreover, the holder 17 has the roller unit driving gear 31a, a roller unit driving gear 31b, the timing belt driving pulley 32, and the shaft 33 are disposed therein. The roller unit driving gear 31a, the roller unit driving gear 31b, the timing belt driving pulley 32, and the shaft 33 represent an example of a driving unit. Moreover, as illustrated in FIGS. 4A and 4B, each roller unit 16 includes the wheels 161, a rail 162, a rack gear 163, and a main body part 164. Herein, two roller units are placed in bilateral symmetry with the center of the long axis direction of the shaft 33 serving as the axis of symmetry. The roller units 16 grasp the C-arm 15 when the rollers of the wheels 161 of each of the right and left roller units 16 engage with the U-shaped rails formed on the lateral faces of the C-arm 15.

The shaft 33 is pivotally supported to be rotatable inside the holder 17. According to the driving force transmitted from a driving source (not illustrated), the shaft 33 performs rotation with the long axis direction representing the rotation axis. Meanwhile, the driving source such as a motor need not be included in the holder 17.

The timing belt driving pulley 32 is a pulley for transmitting the driving force to the C-arm 15. The timing belt driving pulley 32 is fixed to the shaft 33, and rotates accompanying the rotation of the shaft 33. That is, the timing belt driving pulley 32 performs rotation with the shaft 33 representing the rotation axis, and transmits the driving force to the C-arm 15. That results in the sliding movement of the C-arm 15.

Given below is the explanation of a configuration of the imaging unit 10 involved in the sliding movement of the C-arm 15. The C-arm 15 has the shape of a circular arc; and a timing belt (not illustrated) is stretched along the outer periphery, which represents the back surface of the inner surface on which the X-ray tube 12 and the X-ray detector 14 are disposed. The end portions of the timing belt are fixed to the end portions of the C-arm 15, and are extended up to the timing belt driving pulley 32. The timing belt driving pulley 32 is positioned away from the C-arm 15 at a predetermined distance, and is pivotally supported in a rotatable manner by the shaft 33. On the outer surface of the timing belt driving pulley 32, teeth are provided all around at the pitch for enabling engagement with the teeth of the timing belt. Moreover, the timing belt is pressed toward the outer periphery of the C-arm 15 by a timing belt roller (not illustrated). The timing belt roller is rotated by a driving source (not illustrated) according to the rotation of a rotation belt driving pulley 131.

Given below is the explanation about the sliding movement of the C-arm 15. For example, in the X-ray diagnostic apparatus 1, the shaft 33 and the timing belt roller are rotated by a driving source. For example, in the second holding state (see the left-side drawing in FIG. 3), during the sliding movement of the C-arm 15 in the direction indicated by the arrow a1, the timing belt is hauled in due to the rotation of the timing belt driving pulley 32 and the timing belt roller, and is carried in the direction indicated by the arrow a1. As a result, when the timing belt stretched along the outer periphery of the C-arm 15 gets pulled accompanying the rotation of the timing belt driving pulley 32, the C-arm 15 performs the sliding movement in the direction indicated by the arrow a1.

The roller unit driving gear 31a is fixed to the shaft 33, and rotates accompanying the rotation of the shaft 33. That is, the roller unit driving gear 31a rotates along with the shaft 33. The roller unit driving gear 31a engages with the rack gear 163 that is fixed to one of the two roller units 16 which are in bilateral symmetry with the center of the long axis direction of the shaft 33 serving as the axis of symmetry. Then, the roller unit driving gear 31a rotates accompanying the rotation of the shaft 33, and transmits the driving force to the corresponding roller unit 16.

The roller unit driving gear 31b is fixed to the shaft 33, and rotates accompanying the rotation of the shaft 33. That is, the roller unit driving gear 31b rotates along with the shaft 33. The roller unit driving gear 31b engages with the rack gear 163 that is fixed to the other of the two roller units 16 which are in bilateral symmetry with the center of the long axis direction of the shaft 33 serving as the axis of symmetry. Then, the roller unit driving gear 31b rotates accompanying the rotation of the shaft 33, and transmits the driving force to the corresponding roller unit 16.

Figure 5:
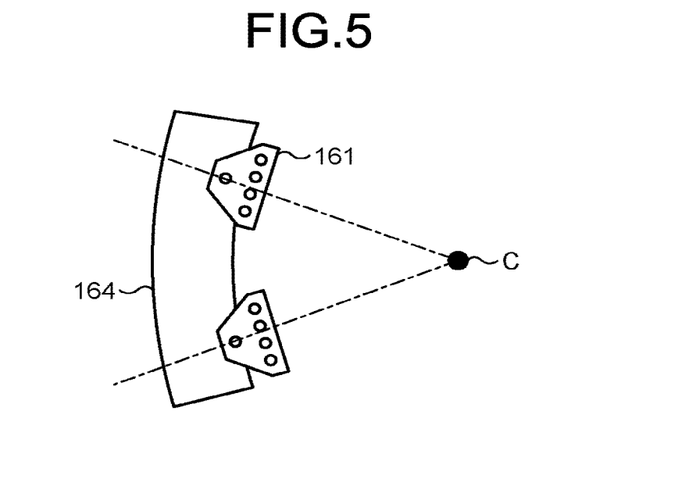
FIG. 5 is a diagram for explaining a roller unit according to the first embodiment.

As explained above, the roller unit driving gears 31a and 31b that are fixed to the shaft 33 transmit the driving force to the respective roller units 16 accompanying the rotation of the shaft 33. With that, the two roller units 16 perform the sliding movement in synchronization. Given below is the explanation of a configuration of the imaging unit 10 involved in the sliding movement of the roller units 16. FIG. 5 is a diagram illustrating a roller unit according to the first embodiment from an identical viewpoint to FIG. 4B. In FIG. 5 are illustrated the wheels of one of the two roller units 16 that are disposed in bilateral symmetry in the holder 17. The main body part 164 represents the main body part of the concerned roller unit 16, and has the shape of a circular arc running along the circular arc of the C-arm 15. For example, the main body part 164 includes two wheels 161 along the circular arc direction. Each wheel 161 includes a plurality of cylindrical rollers that run on the corresponding rail of the C-arm 15. Some part of the wheel 161 is pivotally supported by the main body part 164 to be rotatable up to a predetermined rotation angle.

Figure 6:
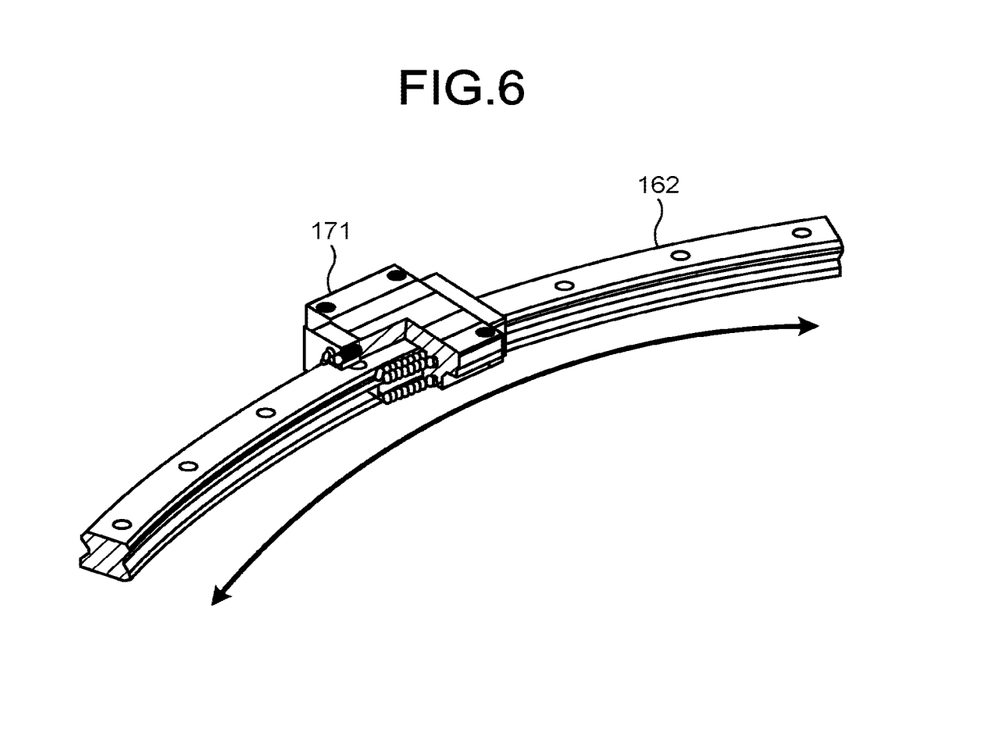
FIG. 6 is a diagram illustrating a block and a rail according to the first embodiment.

The rail 162 is fixed to the main body part 164 of the corresponding roller unit 16. The rail 162 fits in the block 171 that is fixed to the holder 17, and is thus supported by the block 171. That is, since the rail 162 is supported by the block 171, the roller unit 16 is also supported by the holder 17. The rail 162 and the block 171 constitute a linear guide. FIG. 6 is a diagram illustrating the rail 162 and the block 171 according to the first embodiment. As illustrated in FIG. 4B, the rail 162 is formed along the circular arc shape of the main body part 164, and has a U-shaped groove formed on each lateral face thereof. Accompanying the movement of the roller unit 16, the rail 162 moves with respect to the block 171 in the directions indicated by the arrows illustrated in FIG. 6. As a result, accompanying the movement of the roller unit 16, the rail 162 performs the sliding movement in such a way that the position at which it is supported by the block 171 changes. The block 171 represents an example of a supporter.

In FIG. 6 is illustrated an internal structure of the block 171. The block 171 is a housing that fits with the rail 162 via a plurality of internal spherical objects strung together like beads. The block 171 causes the spherical objects to roll so as to enable the sliding movement of the rail 162. Moreover, the block 171 has through holes formed therein as the paths for circulating the spherical objects accompanying the rolling motion. As a result, the block 171 enables a smooth sliding movement of the rail 162. Moreover, regarding the moment load attributed to the projection of the imaging system that occurs accompanying the sliding movement of the rail 162, the block 171 becomes able to resist the moment load with excellent rigidity.

The rack gear 163 is fixed to the roller unit 16, and engages with corresponding the roller unit driving gear 31. More particularly, the rack gear 163 is formed along the circular arc shape of the main body part 164 as illustrated in FIG. 4B, and is disposed on the back surface of the main body part 164. Moreover, in the rack gear 163, teeth are provided at the pitch for enabling engagement with the teeth of the corresponding roller unit driving gear 31. With such a configuration, the rack gear 163 receives the transmission of the driving force from the corresponding roller unit driving gear 31. As a result, the roller unit 16 receives, from the corresponding roller unit driving gear 31, the driving force attributed to the rotation of the shaft 33, and accordingly performs the sliding movement.

Herein, the number of teeth of each roller unit driving gear 31 is set according to the velocity ratio between the C-arm 15 and the corresponding roller unit 16, and according to the number of teeth of the timing belt driving pulley 32. The velocity ratio is set in advance according to the relationship between the maximum movement distance of the C-arm 15 and the maximum movement distance of the roller unit 16. The maximum movement distance represents the maximum value of the distance of the path at the time of performing the movement along a circular arc. For example, the maximum movement distance represents the movement distance for performing the movement along a circular arc at the time of transition from the second holding state to the third holding state. More particularly, the maximum movement distance of the C-arm 15 represents the distance of the path followed during the sliding movement of the C-arm 15 from the second holding state to the third holding state (or from the third holding state to the second holding state). In an identical manner, the maximum movement distance of each roller unit 16 represents the distance of the path followed during the sliding movement of the roller unit 16 from the second holding state to the third holding state (or from the third holding state to the second holding state).

FIRST MODIFICATION EXAMPLE

Figure 7:
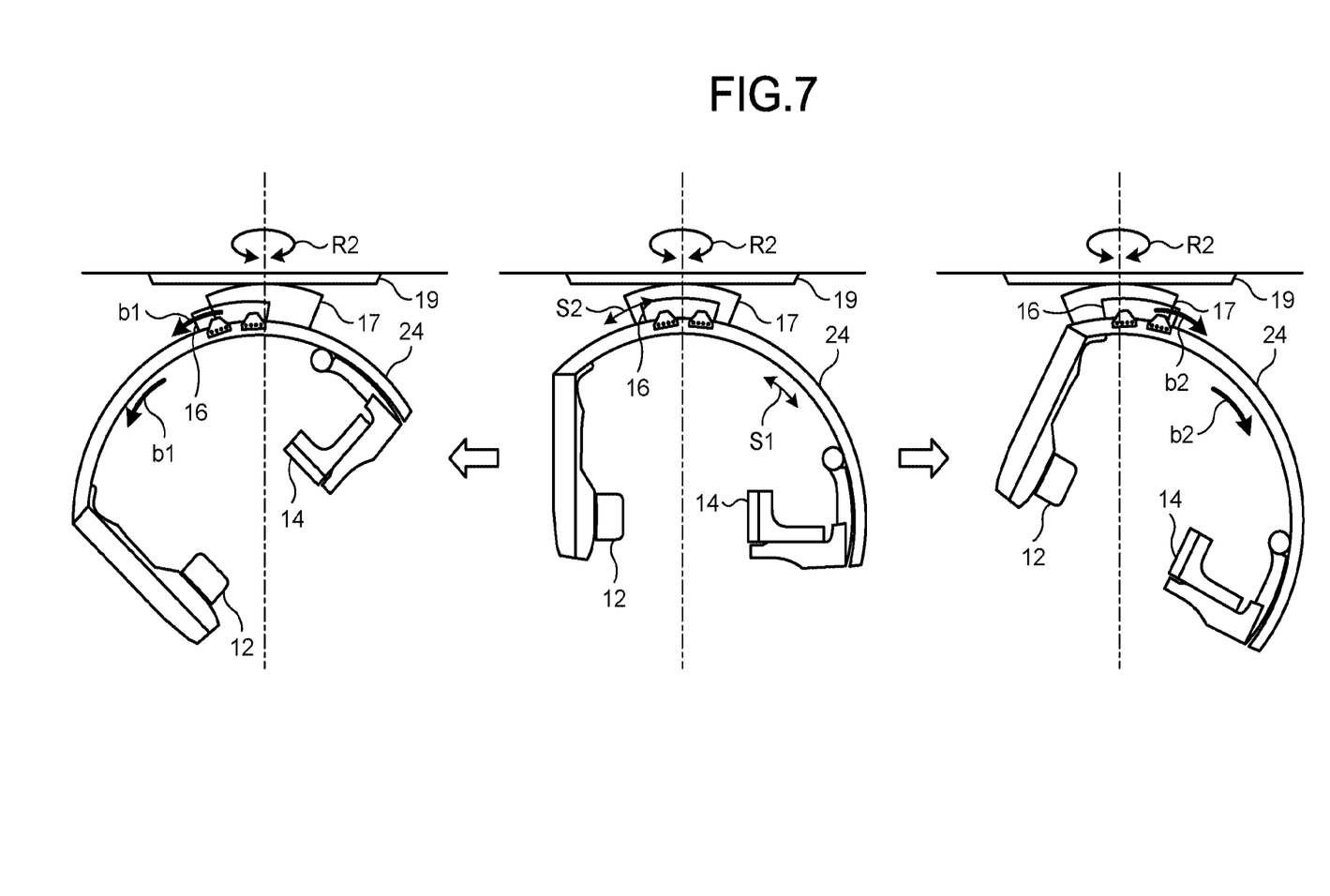
FIG. 7 is a diagram for explaining the X-ray diagnostic apparatus according to a first modification example.

In the first embodiment described above, the explanation is given about the structure in which the suspended-type X-ray diagnostic apparatus 1 includes the C-arm 15. However, the first embodiment is not limited to that structure. Alternatively, the X-ray diagnostic apparatus 1 can include an Ω-arm 24. FIG. 7 is a diagram for explaining the imaging unit 10 and the movements therein according to a first modification example. As illustrated in FIG. 7, the X-ray diagnostic apparatus 1 includes the Ω-arm 24 that corresponds to the C-arm 15 illustrated in FIG. 1. In FIG. 7 is illustrated the transition among three types of Ω-arm holding states occurring in the suspended-type X-ray diagnostic apparatus 1 including an Ω-arm. More particularly, in the central drawing in FIG. 7 is illustrated a first Ω-arm holding state that corresponds to the first holding state illustrated in FIG. 3. In an identical manner, the left-side drawing and the right-side drawing in FIG. 7 correspond to the second holding state and the third holding state, respectively, illustrated in FIG. 3. In the left-side drawing illustrated in FIG. 7, a second Ω-arm holding state is illustrated that is attained when the Ω-arm 24 and the roller units 16 are made to slide in the direction indicated by an arrow b1 from the first Ω-arm holding state, so that the X-ray tube 12 moves away from the holder 17. In the right-side drawing in FIG. 7, a third Ω-arm holding state is illustrated that is attained when the Ω-arm 24 and the roller units 16 are made to slide in the direction indicated by an arrow b2, so that the X-ray tube 12 moves closer to the holder 17.

For example, as illustrated in the second Ω-arm holding state (the left-side drawing in FIG. 7), during the sliding movement of the Ω-arm 24 in the direction indicated by the arrow a1, the roller units 16 perform the sliding movement in the same direction (the direction indicated by the arrow b1) up to the position of being pushed out from the holder 17. In an identical manner, as illustrated in the third Ω-arm holding state (the right-side drawing in FIG. 7), the roller units 16 perform the sliding movement in the same direction (the direction indicated by the arrow b2) up to the position of being pushed out from the holder 17. As a result, in the X-ray diagnostic apparatus 1, as compared to the case in which only the Ω-arm 24 performs the sliding movement in the same direction as explained above, during the sliding movement in which the X-ray tube 12 moves away from the holder 17, the stroke can be widened by the amount equivalent to the amount of sliding movement of the roller units 16.

SECOND MODIFICATION EXAMPLE

Figure 8:
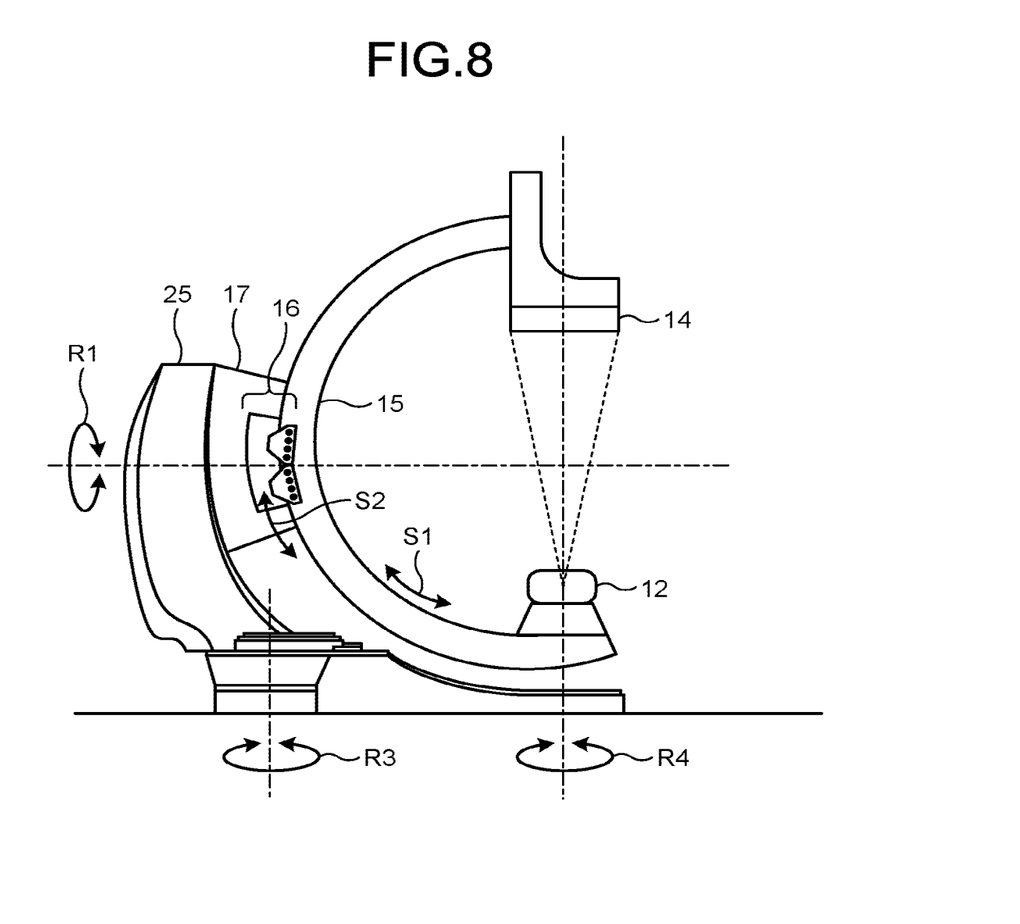
FIG. 8 is a diagram for explaining the X-ray diagnostic apparatus according to a second modification example.

In the first embodiment described above, the explanation is given about the case in which the X-ray diagnostic apparatus 1 is of the suspended type. However, the embodiment is not limited to that case. Alternatively, the imaging unit 10 can be of the floor-standing type in which the support is provided by the floor. FIG. 8 is a diagram for explaining the imaging unit 10 and the movements therein according to a second modification example. As illustrated in FIG. 8, the floor-standing X-ray diagnostic apparatus 1 includes a stand 25 that is installed on the floor and that supports the holder 17. The upper portion of the stand 25 (the portion supporting the holder 17) is pivotally supported around a rotation axis R3 in a rotatable manner. Moreover, the lower portion of the stand 25 (the portion in contact with the floor surface) is pivotally supported around a rotation axis R4 in a rotatable manner, and causes gyration of the stand 25 and the holder 17 in an integrated manner on the floor surface. In FIG. 8, the holding state of the C-arm 15 corresponds to the first holding state illustrated in FIG. 3.

Given below is the explanation of the movements occurring in the floor-standing X-ray diagnostic apparatus 1. In an identical manner to the suspended-type X-ray diagnostic apparatus 1 according to the first embodiment, the roller units 16 that hold the C-arm 15 perform the sliding movement in the same direction as the direction of the sliding movement of the C-arm 15. With that, in the floor-standing X-ray diagnostic apparatus 1, the stroke of the C-arm can be widened. More particularly, due to the same driving force, the C-arm 15 and the roller unit 16 perform the sliding movement in circular arc directions indicated by arrows S1 and S2, respectively, illustrated in FIG. 8; so that either the X-ray tube 12 or the X-ray detector 14 moves away from the holder 17. As a result, in an identical manner to the suspended-type X-ray diagnostic apparatus 1, in the floor-standing X-ray diagnostic apparatus 1 too, as compared to the case in which only the C-arm 15 performs the sliding movement in the same direction as explained above, the stroke can be widened by the amount equivalent to the amount of sliding movement of the roller unit 16.

As explained above, according to the first embodiment described above, the C-arm 15 has the shape of a circular arc. The C-arm 15 supports, at one end thereof, the X-ray tube 12 that emits X-rays onto the subject; and supports, at the other end thereof, the X-ray detector 14 that detects the X-rays which have passed through the subject. The roller units 16 grasp the C-arm 15 in a movable manner in the circular direction arc. The holder 17 supports the roller units 16 in a movable manner in the circular arc direction of the C-arm 15. The driving unit is disposed in the holder 17. The driving unit causes the roller units 16 to move, and causes the C-arm 15 to relatively move with respect to the roller units 16. The ceiling-type rotating arm 18 is orthogonal to the rotation axis involved in the movement of the C-arm 15 in the circular arc direction, and rotatably holds the holder 17 with the axis substantially orthogonal to the vertical direction serving as the rotation axis. As a result, in addition to implementing the sliding movement of the C-arm 15, the sliding movement of the roller units 16 is also implemented. That is, the stroke of the C-arm 15 can be widened by the amount equivalent to the amount of sliding movement of the roller units 16. That enables achieving expansion in the slidable range of the C-arm 15.

Figure 9:
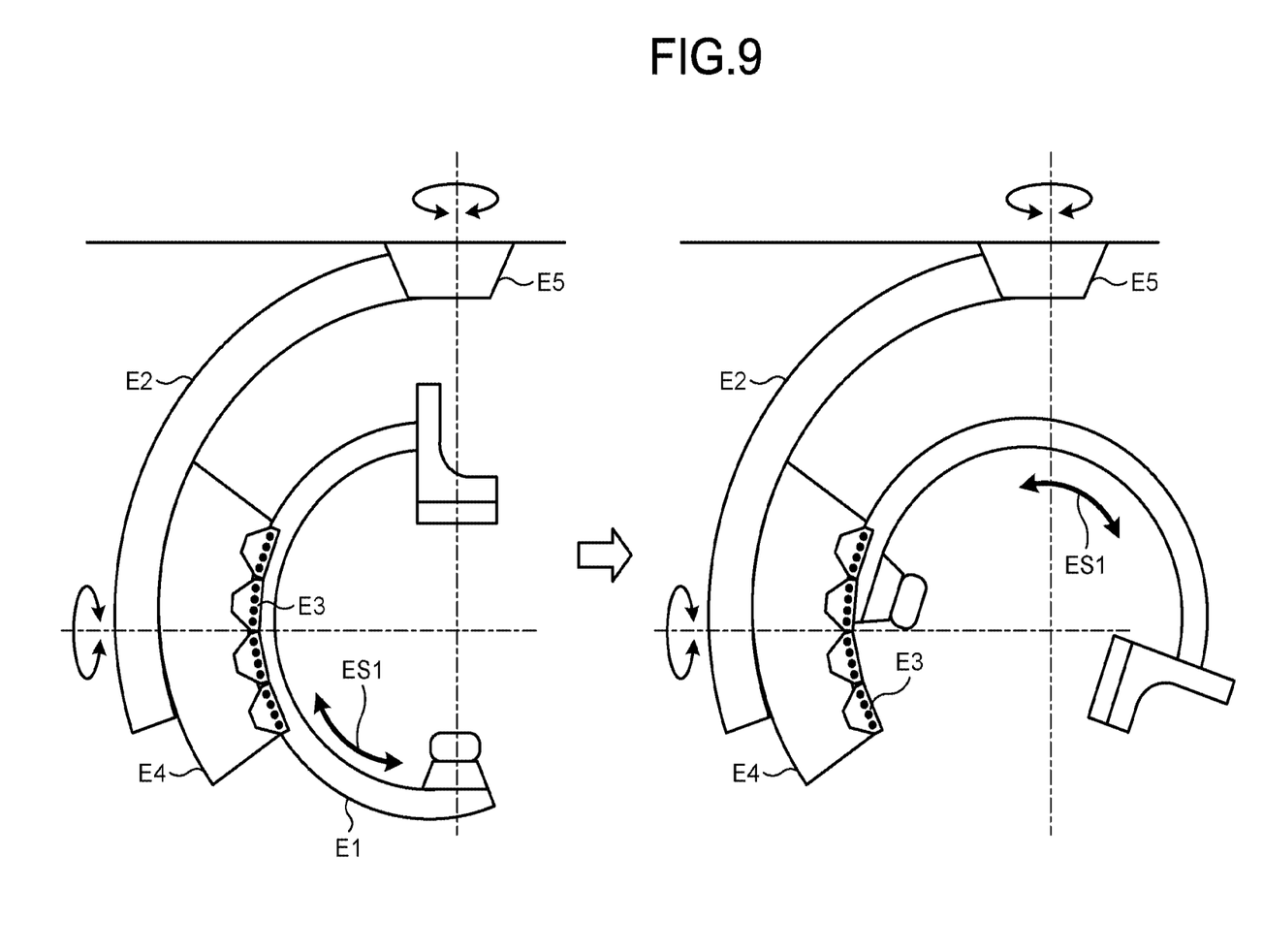
FIG. 9 is a diagram for explaining a structure in which the size of a holder is increased and a plurality of wheels is included therein.

Meanwhile, other than the configuration of the X-ray diagnostic apparatus 1 according to the first embodiment, it is also possible to think of a structure in which the size of the holder is increased so that the number of wheels fixed inside the holder can be increased and it becomes possible to transfer the C-arm on the wheels. However, that structure may lead to an increase in the size of the X-ray diagnostic apparatus. In FIG. 9 is illustrated an example of an X-ray diagnostic apparatus having the structure in which the size of the holder is increased and a plurality of wheels is included therein. As illustrated in FIG. 9, a C-arm E1 performs the sliding movement in the direction indicated by an arrow ES1 and on four wheels included in a holder E4. In contrast to this structure, in the first embodiment, the holder is prevented from increasing in size, thereby enabling prevention of an increase in the size of the X-ray diagnostic apparatus.

Moreover, according to the first embodiment described above, the driving unit drives the movement of the C-arm 15 and the movement of the roller units 16 with the same driving force. That eliminates the need to install separate driving sources for moving the C-arm 15 and moving the roller units 16. Thus, the configuration of the X-ray diagnostic apparatus 1 enables avoiding complexity of the internal structure of the imaging unit 10. That enables achieving expansion of the stroke of the C-arm while holding down an increase in the size of the X-ray diagnostic apparatus 1.

Furthermore, according to the first embodiment described above, the rotation axis of the timing belt driving pulley 32 using which the driving unit transmits the driving force to the C-arm 15 is formed on the same axis as the rotation axis of the roller unit driving gears 31 using which the driving unit transmits the driving force to the roller units 16. As a result, the driving force that is transmitted to the shaft 33 can be transmitted to the C-arm 15 and the roller units 16. Thus, in the X-ray diagnostic apparatus 1, the structure regarding the driving of the roller units 16 is disposed to be linked with the driving of the C-arm 15. Hence, it becomes possible to further avoid complexity in the internal structure of the imaging unit 10. In turn, it becomes possible to hold down an increase in the size of the X-ray diagnostic apparatus 1.

Moreover, according to the first embodiment, the driving unit moves the C-arm 15 and the roller units 16 at the velocity ratio corresponding to the relationship between the maximum movement distance of the C-arm 15 and the maximum movement distance of the roller units 16. Hence, in the X-ray diagnostic apparatus 1, the C-arm 15 and the roller units 16 can be made to slide in a coordinated manner, while catering to the respective movement distances different from each other. Thus, in the X-ray diagnostic apparatus 1, the C-arm 15 and the roller units 16 can be made to slide in an appropriately coordinated manner.

Furthermore, according to the first embodiment, the driving unit transmits the driving force to the C-arm 15 and moves the C-arm 15; as well as transmits the driving force to the roller units 16 via the roller unit driving gears 31, which have teeth in proportion to the velocity ratio, and accordingly moves the roller units 16. As a result, in tandem with the sliding movement of the C-arm 15, the roller units 16 can perform the sliding movement according to the rotation of the roller unit driving gears 31. Thus, in the X-ray diagnostic apparatus 1, an appropriately coordinated movement of the C-arm 15 and the roller units 16 can be achieved with ease.

Moreover, according to the first embodiment, the holder 17 includes a supporting member. The roller units 16 have rails in the shape of a circular arc, and the rails are supported by the supporting member. The position at which the rails are supported by the supporting member changes accompanying the movement of the roller units 16. Hence, in regard to the sliding movement of the C-arm 15 and the roller units 16, the load created as a result of pushing out the imaging system from the holder 17 is supported by the slidable engagement of the rails 162 and the block 171. That enables achieving a smooth sliding movement. For that reason, it becomes possible to reduce the vibrations of the imaging system attributed to the sliding movement, while eliminating the need to add a complex internal structure for holding down the vibrations of the imaging system. Thus, it becomes possible to hold down an increase in the size of the X-ray diagnostic apparatus 1.

Other Embodiment

Figure 10:
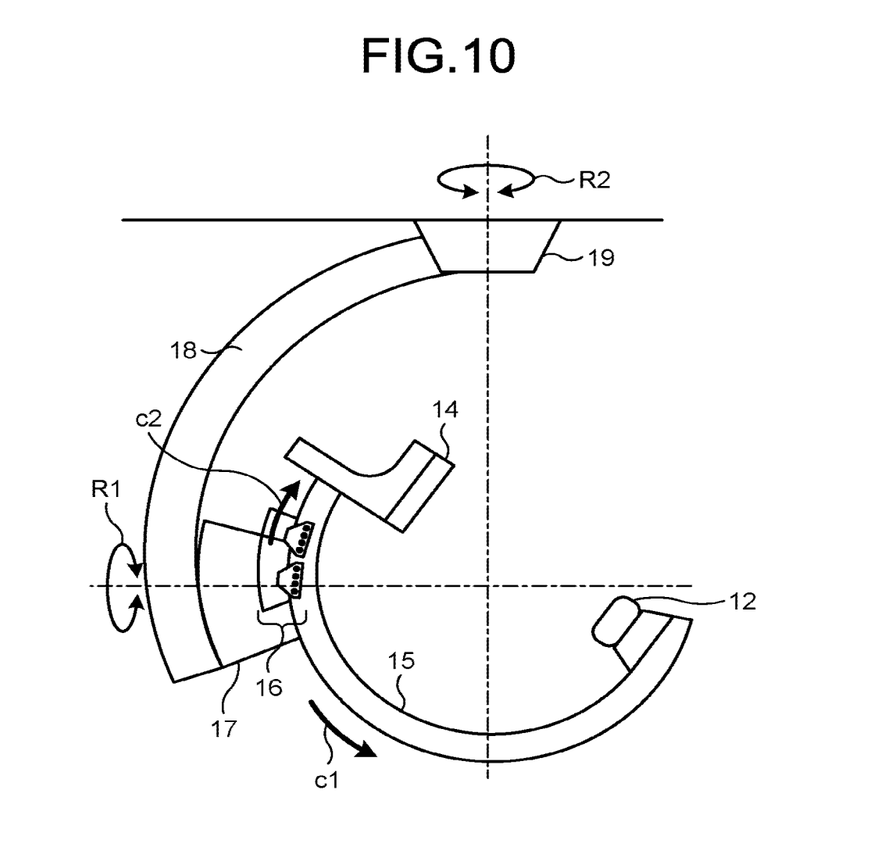
FIG. 10 is a diagram illustrating an exemplary configuration of the imaging unit in the X-ray diagnostic apparatus according to another embodiment.

In the first embodiment, the explanation is given for the case in which the C-arm 15 and the roller units 16 perform the sliding movement in the same circular arc direction. However, the embodiment is not limited to that case. Alternatively, the C-arm 15 and the roller units 16 can independently perform the sliding movement in circular arc directions. FIG. 10 is a diagram illustrating an exemplary configuration of the imaging unit 10 in the X-ray diagnostic apparatus 1 according to another embodiment. In the X-ray diagnostic apparatus 1 according to the other embodiment, as compared to the first embodiment, the control performed by the control function 201 in the processing circuitry 20 is different and the driving unit is also different. The following explanation is focused on those differences.

In addition to having the control function 201 according to the first embodiment, the control function 201 according to the other embodiment also has a function for setting up the amount of movement of the roller units 16 based on the positional relationship between the C-arm 15 and the roller units 16. The amount of movement represents the distance of the path followed during the sliding movement along a circular arc. Moreover, regarding the control function 201, in addition to calculating the amount of movement based on the positional relationship between the C-arm 15 and the roller units 16, the control function 201 can also change the calculated amount of movement in response to an operation performed by the user via the input interface 21. Alternatively, the user can set, in advance, a rough indication of the amount of movement; so that the control function 201 can calculate the amount of movement based on the preset amount.

The driving unit applies different driving forces for causing the sliding movement of the C-arm 15 and for causing the sliding movement of the roller units 16, and thus implements independent sliding movements. For example, the timing belt driving pulley 32, which is involved in the driving of the C-arm 15, and the roller unit driving gears 31, which are involved in the driving of the roller units 16, are not driven by the same driving force, and perform rotation after independently receiving the transmission of a driving force. As a result, the roller units 16 become able to perform the sliding movement in a different direction than the direction of the sliding movement of the C-arm 15.

For example, the control function 201 controls the driving unit that applies a driving force to the C-arm 15, and causes the C-arm 15 to perform the sliding movement in the direction indicated by an arrow c1 illustrated in FIG. 10. Then, the control function 201 controls the driving unit that applies a driving force to the roller units 16, and causes the roller units 16 to perform the sliding movement in the direction indicated by an arrow c2 illustrated in FIG. 10. For example, when the sliding movement causes the X-ray tube 12 to move away from the holder 17, the X-ray tube 12 might have a large mass thereby resulting in a large moment load. In that case, the control function 201 collects the positional relationship between the C-arm 15 and the roller units 16, and decides on the amount of sliding movement of the roller units 16 in the direction indicated by the arrow c2. Then, the driving unit causes the roller units 16 to perform the sliding movement in the direction indicated by the arrow c2 according to the decided amount of sliding movement of the roller units 16. As a result, in the X-ray diagnostic apparatus 1, the moment load of the X-ray tube 12 gets supported.

Herein, the explanation is given about the case in which the direction of the sliding movement of the C-arm 15 and the direction of the sliding movement of the roller units 16 are opposite directions as indicated by the arrows c1 and c2 illustrated in FIG. 10. However, the embodiment is not limited to that case. Alternatively, the C-arm 15 and the roller units 16 can perform the sliding movement in the same direction. In that case, the C-arm 15 and the roller units 16 can perform the sliding movement with different amounts of movement without any coordination therebetween. For example, the driving unit causes the roller units 16 to perform the sliding movement in the direction indicated by the arrow c1 and according to the amount of sliding movement decided by the control function 201. As a result, in the X-ray diagnostic apparatus 1, it becomes possible to resist the moment load, which is generated in the imaging unit 10, in an excellent manner.

As explained above, according to the other embodiment, the driving unit moves the roller units 16 independently from the movement of the C-arm 15 and with a different driving force than the driving force applied for the sliding movement of the C-arm 15. As a result, the moment load generated in the imaging system due to the movement of the C-arm 15 can be resisted in an excellent manner because of the independent movement of the roller units 16. Thus, in the X-ray diagnostic apparatus 1, the support balance of the imaging unit 10 in regard to the sliding movement of the C-arm 15 can be maintained in a better way, thereby making it possible to easily expand the slidable range of the C-arm 15.

Moreover, according to the other embodiment, based on the positional relationship between the C-arm 15 and the roller units 16, the control function 201 sets up the amount of movement of the roller units 16. As a result, the roller units 16 can be moved to arbitrary positions, thereby making it possible to resist the moment load generated in the imaging system due to the movement of the C-arm 15. Thus, in the X-ray diagnostic apparatus 1, the support balance of the imaging unit 10 in regard to the sliding movement of the C-arm 15 can be maintained in a better way, thereby making it possible to easily expand the slidable range of the C-arm 15.

Meanwhile, the term "processor" used in the description of the embodiments implies, for example, a central processing unit (CPU), or a graphics processing unit (GPU), or an application specific integrated circuitry (ASIC), or a programmable logic device (such as a simple programmable logic device (SPLD), or a complex programmable logic device (CPLD), or a field programmable gate array (FPGA)). Moreover, instead of storing a computer program in the memory circuitry 23, it can be directly incorporated into the circuitry of a processor. In that case, the processor reads the computer program incorporated in the circuitry and executes it so that the functions get implemented. Meanwhile, the processors according to the embodiments are not limited to be configured using a single circuitry on a processor-by-processor basis. Alternatively, a single processor can be configured by combining a plurality of independent circuitries, and the corresponding functions can be implemented.

A computer program executed by a processor is stored in advance in a read only memory (ROM) or a memory circuit. Alternatively, the computer program can be recorded as an installable file or an executable file in a non-transitory computer-readable recording medium such as a compact disk read only memory (CD-ROM), a flexible disk (FD), a compact disk recordable (CD-R), or a digital versatile disk (DVD). Still alternatively, the computer program can be stored in a downloadable manner in a computer that is connected to a network such as the Internet. For example, the computer program is configured using modules of the processing functions explained above. As far as the actual hardware is concerned, a CPU reads the computer program from a memory medium such as a ROM and executes it, so that the modules get loaded and generated in a main memory device.

In the embodiments and the modification examples described above, the constituent elements of the device illustrated in the drawings are merely conceptual, and need not be physically configured as illustrated. The constituent elements, as a whole or in part, can be separated or integrated either functionally or physically based on various types of loads or use conditions. The processing functions implemented by the device are entirely or partially implemented by the CPU or by computer programs that are analyzed and executed by the CPU, or are implemented as hardware by wired logic.

Of the processes described in the embodiments, all or part of the processes explained as being performed automatically can be performed manually. Similarly, all or part of the processes explained as being performed manually can be performed automatically by a known method. The processing procedures, the control procedures, specific names, various data, and information including parameters described in the embodiments or illustrated in the drawings can be changed as required unless otherwise specified.

According to at least one of the embodiments described above, it is possible to expand the slidable range of the arm while holding down an increase in the apparatus size.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
    an arm
        that has a shape of a circular arc,
        that, at one end thereof, supports an X-ray tube which emits X-rays onto a subject, and
        that, at another end thereof, supports an X-ray detector which detects X-rays that have passed through the subject;
    a first holder that grasps the arm in a slidable manner in a circular arc direction;
    a second holder that supports the first holder in a slidable manner in the circular arc direction;
    a driver
        that is disposed in the second holder,
        that moves the first holder, and
        that, at a same time, relatively moves the arm with respect to the first holder; and
    a third holder that is orthogonal to a rotation axis involved in movement of the arm in the circular arc direction and that holds the second holder in a rotatable manner with a rotation axis substantially orthogonal to a vertical direction, wherein
    the first holder slides in the same circular arc direction as the arm up to a position of being pushed out from the second holder.

2. The X-ray diagnostic apparatus according to claim 1, wherein the driver drives sliding movement of the arm and sliding movement of the first holder with a same driving force.

3. The X-ray diagnostic apparatus according to claim 1, wherein the driver moves the arm and the first holder at a velocity ratio corresponding to a relationship between a maximum movement distance of the arm and a maximum movement distance of the first holder.

4. The X-ray diagnostic apparatus according to claim 3, wherein the driver
    transmits a driving force to the arm and drives the arm, and
    transmits the driving force to the first holder via a gear having teeth in proportion to the velocity ratio, and drives the first holder.

5. The X-ray diagnostic apparatus according to claim 4, wherein, in the driver, a pulley for transmitting the driving force to the arm has a rotation axis on a same axis as a rotation axis of the gear for transmitting the driving force to the first holder.

6. The X-ray diagnostic apparatus according to claim 1, wherein
    the second holder includes a supporter,
    the first holder includes a rail that is supported by the supporter and that has a shape of a circular arc, and
    a position at which the rail is supported by the supporter changes accompanying sliding movement of the second holder.

7. The X-ray diagnostic apparatus according to claim 1, wherein the driver slides the first holder in an independent manner from sliding movement of the arm and using a driving force different than a driving force applied for the sliding movement of the arm.

8. The X-ray diagnostic apparatus according to claim 7, further comprising processing circuitry configured to set an amount of sliding movement of the first holder based on a positional relationship between the arm and the first holder.

9. An X-ray diagnostic apparatus comprising:
    an arm
        that has a shape of a circular arc,
        that, at one end thereof, supports an X-ray tube which emits X-rays onto a subject, and
        that, at another end thereof, supports an X-ray detector which detects X-rays that have passed through the subject;
    a first holder that grasps the arm in a slidable manner in a circular arc direction;
    a second holder that supports the first holder in a slidable manner in the circular arc direction;
    a driver
        that is disposed in the second holder,
        that moves the first holder, and
        that, at a same time, relatively moves the arm with respect to the first holder; and
    a third holder that holds the second holder in rotatable manner with axis substantially orthogonal to vertical direction serving as rotation axis, wherein
    the first holder slides in the same circular arc direction as the arm up to a position of being pushed out from the second holder.

* * * * *